United States Patent
Hsiao et al.

(10) Patent No.: US 9,498,553 B2
(45) Date of Patent: *Nov. 22, 2016

(54) AROMA-DIFFUSING HEATING DEVICE USING A REPLACEABLE AROMA CAPSULE AND THE AROMA CAPSULE

(71) Applicant: SERENE HOUSE INTERNATIONAL ENTERPRISE LTD., Tortola (VG)

(72) Inventors: Ming Jen Hsiao, Miaoli County (TW); Peter Wirz, Luzern (CH)

(73) Assignee: SERENE HOUSE INTERNATIONAL ENTERPRISE LTD., Tortola (VG)

( * ) Notice: Subject to any disclaimer, the term of this patent is extended or adjusted under 35 U.S.C. 154(b) by 481 days.

This patent is subject to a terminal disclaimer.

(21) Appl. No.: 14/042,162

(22) Filed: Sep. 30, 2013

(65) Prior Publication Data

US 2014/0072286 A1 Mar. 13, 2014

Related U.S. Application Data

(63) Continuation-in-part of application No. 13/549,490, filed on Jul. 15, 2012, now Pat. No. 8,668,885, and a continuation-in-part of application No. 13/549,493, filed on Jul. 15, 2012, now abandoned, and a continuation-in-part of application No. 13/658,820, filed on Oct. 24, 2012, now abandoned.

(51) Int. Cl.
| | |
|---|---|
| F22B 29/06 | (2006.01) |
| F22B 35/06 | (2006.01) |
| A01G 13/06 | (2006.01) |
| A61L 9/03 | (2006.01) |

(52) U.S. Cl.
CPC .................................. A61L 9/03 (2013.01)

(58) Field of Classification Search
None
See application file for complete search history.

(56) References Cited

U.S. PATENT DOCUMENTS

| | | | |
|---|---|---|---|
| 5,647,052 A | 7/1997 | Patel et al. | |
| 6,413,476 B1 | 7/2002 | Barnhart | |
| 7,572,412 B2* | 8/2009 | Yang .................... | A61L 9/122 392/386 |
| 8,772,675 B2* | 7/2014 | Juarez .................. | H05B 3/26 219/209 |
| 9,211,355 B2* | 12/2015 | Thompson ............ | A61L 9/03 |
| 2005/0016985 A1* | 1/2005 | Haas ..................... | A61L 9/03 219/438 |
| 2005/0184045 A1* | 8/2005 | Shimizu ................ | A61L 9/03 219/474 |
| 2008/0279731 A1* | 11/2008 | Goreham .............. | A61L 9/037 422/125 |
| 2010/0096376 A1* | 4/2010 | Hsiao ................... | A61L 9/03 219/201 |
| 2010/0260646 A1* | 10/2010 | Jorgensen ............. | A61L 9/035 422/125 |
| 2011/0110824 A1* | 5/2011 | Hsiao ................... | A61L 9/035 422/125 |

* cited by examiner

*Primary Examiner* — Thor Campbell
(74) *Attorney, Agent, or Firm* — Ming Chow; Sinorica, LLC (57) ABSTRACT

An aroma-diffusing heating device includes a heating base, and an aroma capsule detachably accommodated in the heating base and heatable by the heating base to give off fragrance. The aroma capsule includes a heat-transfer container defining a top opening, an aromatic substance held in the heat-transfer container, and a breathing film bonded to the heat-transfer container in the top opening of the heat-transfer container. The breathing film has open spaces defined therein.

18 Claims, 10 Drawing Sheets

AROMA-DIFFUSING HEATING DEVICE USING A REPLACEABLE AROMA CAPSULE AND THE AROMA CAPSULE

CROSS-REFERENCE TO RELATED APPLICATIONS

The present invention is a continuation-in-part of, and claims priorities to the U.S. patent application Ser. No. 13/549,490 filed on Jul. 15, 2012, U.S. patent application Ser. No. 13/549,493 filed on Jul. 15, 2012, and U.S. patent application Ser. No. 13/658,820 filed on Oct. 24, 2012.

FIELD OF THE INVENTION

The present invention relates to scent releasing devices and more specifically, to an aroma-diffusing heating device that uses a replaceable aroma capsule. The invention relates also to the aroma capsule.

DESCRIPTION OF THE RELATED ART

In modern society, in order to remove the smell in the air, or to enrich the spice of life, many people started using fragrance products (for example, aromatic wax, essential oils). When in use, a user needs to remove the aromatic wax from the aromatic wax container and put it in an accommodation chamber in a heater, and then electrically conduct the heater to heat the aromatic wax, causing the aromatic wax to give off fragrance.

The aforesaid application method has drawbacks. During application, the user must remove the aromatic wax from the aromatic wax container and then put the aromatic wax in the accommodation chamber in the heater carefully, avoiding direct contact of the hands with the aromatic wax. After the aromatic wax having been put in the accommodation chamber in the heater, the aromatic wax may be forced out of the heater accidentally upon an impact. Further, after the aromatic wax in the accommodation chamber in the heater is used up, the user needs to clean the accommodation chamber. If the accommodation chamber is not cleaned after each use, a new supply of aromatic wax will be mixed with the residual aromatic wax in the accommodation chamber, giving a bad smell. Further, if the accommodation chamber is formed of a fragile material (for example, ceramics), it may be broken easily during cleaning.

Therefore, it is desirable to provide an aroma-diffusing design that eliminates the drawbacks of the aforesaid prior art design.

SUMMARY OF THE INVENTION

The present invention has been accomplished under the circumstances in view. It is therefore an object of the present invention to provide an aroma-diffusing heating device, which is configured to heat an aroma capsule to give off fragrance, wherein the aroma capsule is replaceable with a new one when used up.

To achieve this and other objects of the present invention, an aroma-diffusing heating device comprises a heating base defining a top accommodation open chamber, heating base can be made from ceramic, wooden, glass or plastic, and an aroma capsule detachably accommodated in the top accommodation open chamber of the heating base and heatable by the heating base to give off fragrance. The aroma capsule includes a heat-transfer container defining a top opening, an aromatic substance, for example, solid aromatic wax held in the heat-transfer container, and a breathing film bonded to said heat-transfer container to keep said aromatic substance in said heat-transfer container, said breathing film having open spaces defined therein. The aroma substance is heated by aroma-diffusing heating device and disperses scent. It the aroma-diffusing heating device and the aroma capsule are toppled by chance, the melted scented wax is blocked by the breathing film form flowing to a region outside of the aroma-diffusing heating device, the aroma-diffusing heating device is thus safe to use.

Further, the aroma capsule further comprises a sealing film bonded to said heat-transfer container to seal said aromatic substance in said heat-transfer container.

Further, the aroma capsule is configured to fit the shape of the top accommodation open chamber of the heating base.

Further, the heating base comprises a top flange raised from the top wall thereof.

Further, the heat-transfer container of the aroma capsule comprises a rim extending around the top opening.

Further, the aroma-diffusing heating device further comprises: a bottom cover disposed on a bottom of the heating base; a power circuit board disposed on the bottom cover; a protection cover supported by the bottom cover; a resistor placed on the protection cover and electrically connected to the power circuit board for generating heat; and a receiving unit, the receiving unit center defining said top accommodation open chamber, the receiving unit further comprises a heat conductive unit disposed at top accommodation open chamber inner side thereof, the heat conductive unit having one side in contact with one side of the resistor, the heat conductive unit reverse side in contact with the aroma capsule.

The invention also provides an aroma capsule, comprising: a heat-transfer container defining a top opening; an aromatic substance held in said heat-transfer container; and a breathing film bonded to said heat-transfer container over said top opening of said heat-transfer container above said aromatic substance in said heat-transfer container, said breathing film having open spaces defined therein.

Further, the aroma capsule comprises a sealing film bonded to said heat-transfer container over the top opening to seal said aromatic substance in said heat-transfer container and said breathing film under said sealing film.

Further, the aroma capsule comprises a breathing film and/or a sealing film bonded to said rim of the heat-transfer container to seal said aromatic substance in said heat-transfer container and said breathing film under said sealing film.

In an embodiment, an aroma capsule, comprising: a heat-transfer container defining a top opening; an aromatic substance held in said heat-transfer container; and a sealing film bonded to said heat-transfer container over the top opening to seal said aromatic substance in said heat-transfer container.

DETAILED DESCRIPTION OF THE PREFERRED EMBODIMENT

Referring to FIGS. 1-4, an aroma-diffusing heating device 1 in accordance with the present invention is shown having an aroma capsule 12 therein. The aroma-diffusing heating device 1 comprises a heating base 10 defining a top accommodation open chamber 100, said aroma capsule 12 detachably accommodated in the top accommodation open chamber 100 and heatable by said heating base to give off fragrance.

The aroma capsule 12 comprises a heat-transfer container 120 contact with the heating base 10 and defining a top opening 1200, an aromatic substance 122 (for example, aromatic wax in this preferred embodiment, aromatic block, essential oil, or perfume) put in the heat-transfer container 120, and a breathing film 126 bonded to said heat-transfer container 120 over top opening 1200 to keep said aromatic substance 122 in said heat-transfer container 120, said breathing film 126 having open spaces 1263 defined therein, the aroma substance 122 is heated by aroma-diffusing heating device 1 and disperses scent through the open spaces 1263. If the aroma-diffusing heating device 1 and the aroma capsule 12 are toppled by chance, the melted scented wax is blocked by the breathing film 126 form flowing to a region outside of the aroma-diffusing heating device 1, the aroma-diffusing heating device 1 is thus safe to use.

In an embodiment, the aroma capsule 12 further comprises a sealing film 124 bonded to the heat-transfer container 120 over top opening 1200 to seal the aromatic substance 122 in the heat-transfer container 120, maintaining the quality of the aromatic substance 122 and said breathing film 126 under said sealing film 124.

In an embodiment, said heat-transfer container 120 of said aroma capsule 12 comprises a rim 1202 extending around said top opening 1200, and said sealing film 124 is bonded to said rim 1202 of said heat-transfer container 120 and said breathing film 126 under said sealing film 124.

In an embodiment, said aroma capsule 12 further comprises a rim 1202 extending around said top opening 1200, and said breathing film 126 has a border edge 1261, the border edge 1261 can be bonded to the rim 1202 of the heat-transfer container 120 above the top opening 1200.

In an embodiment, the heat-transfer container 120 is an aluminum foil bowl.

During application, the user simply needs to remove the sealing film 124 from the rim 1202 of the heat-transfer container 120 and then electrically conducting the heating base 10 to heat the aromatic substance 122, causing the aromatic substance 122 to give off fragrance into the outside open air.

According to the present invention, the heating base 10 is configured to heat the aromatic substance 122 to about 40~70° C., or preferably 50~55° C. Within this temperature range, commercial aromatic substances can give off fragrance without destroying the quality. Further, under this temperature range of 40~70° C., the heat-transfer container 120 is maintained intact and can effectively transfer heat from the heating base 10 to the aromatic substance 122 (aromatic wax). The heat-transfer container 120 can be selected from the material group of ceramics, metals, and hard plastics. Preferably, the heat-transfer container 120 is made from a light metal, for example, aluminum foil for the advantages of light weight, high toughness and high thermal conductivity, avoiding the disadvantage of high fragileness of pottery bowls and glass containers. Further, the sealing film 124 seals the aromatic substance 122 in the top opening 1200, maintaining the quality of the aromatic substance 122.

Figure 5:
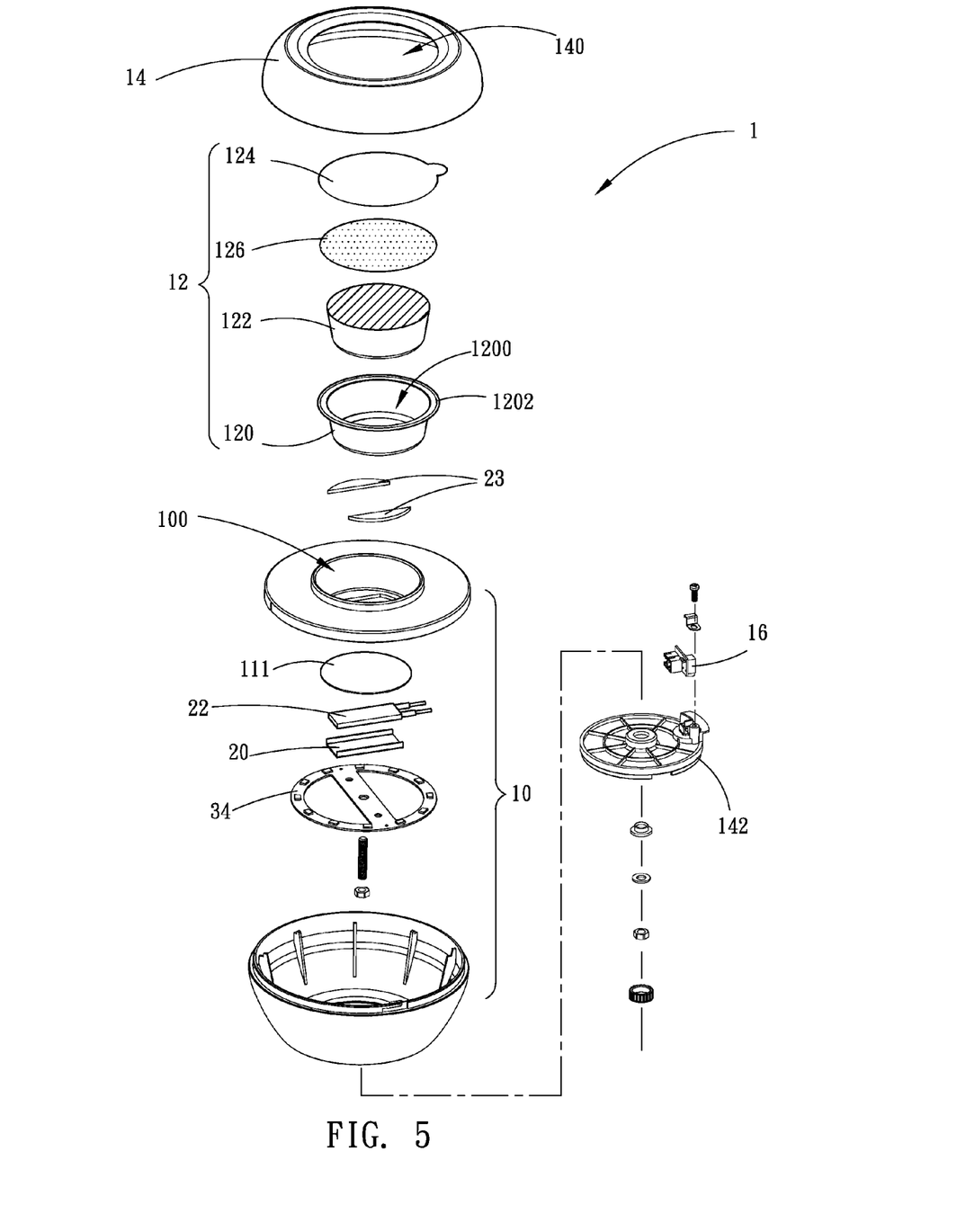
FIG. 5 is an exploded view of a aroma-diffusing heating device having a removable aroma capsule for an aroma substance to be contained therein.
Figure 6:
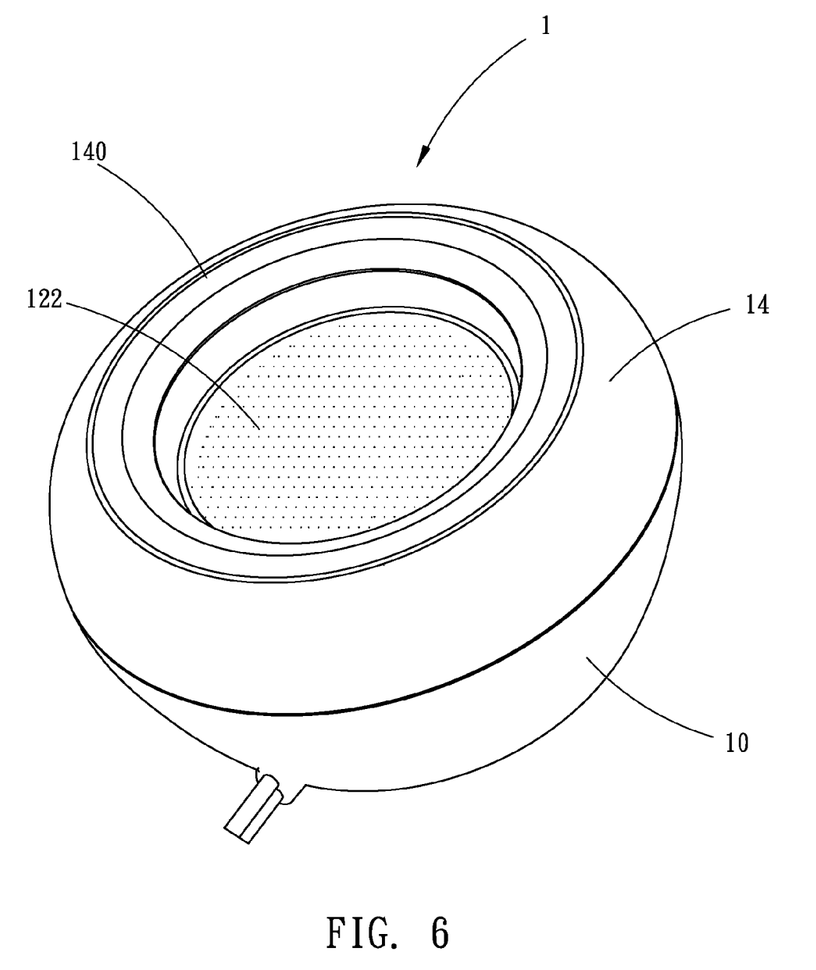
FIG. 6 is an elevational view of an aroma-diffusing heating device in accordance with the present invention.
Figure 7:
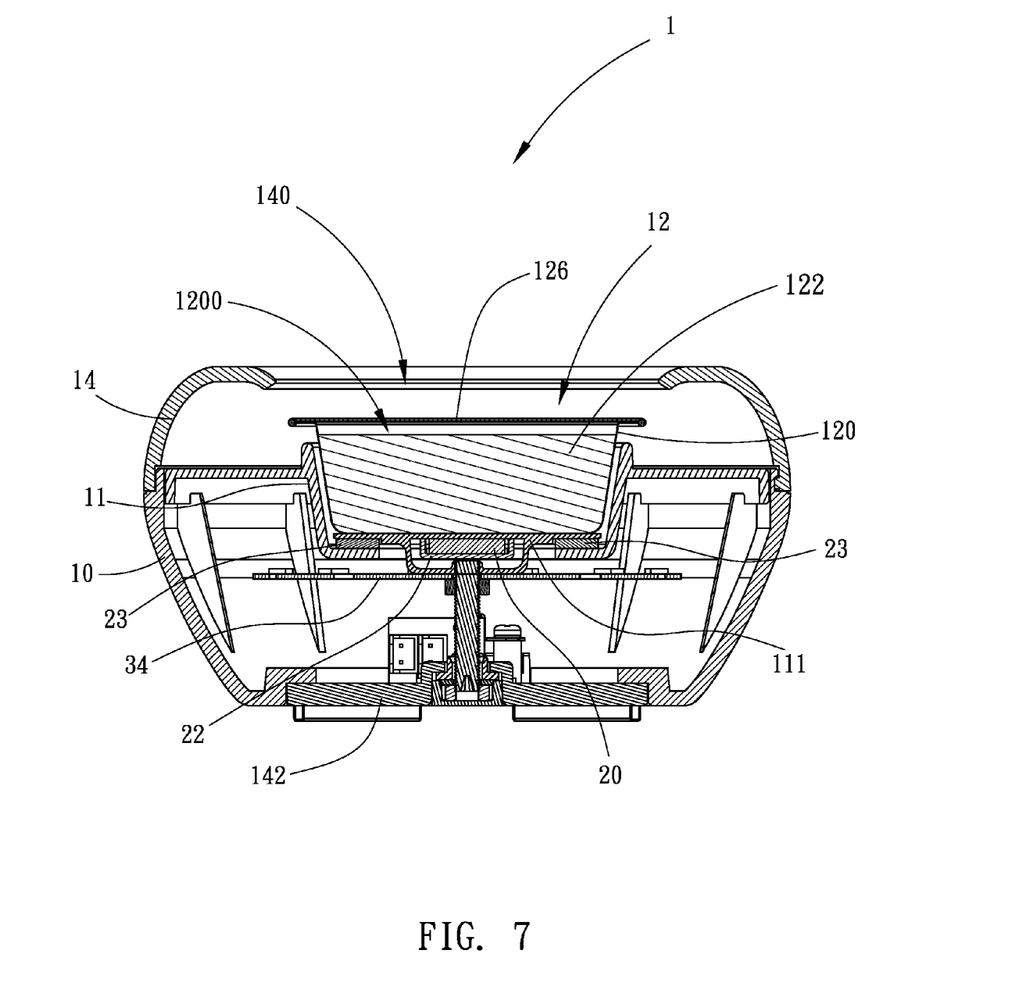
FIG. 7 is a cross-sectional view of the aroma-diffusing heating device shown in FIG. 6, respectively.

Referring to FIGS. 5-7, the aroma-diffusing heating device 1 further comprises a bottom cover 142 disposed on a bottom of the heating base 10, a power circuit board 16 disposed on the bottom cover 142; a protection cover 20 supported by the bottom cover 142, a resistor 22 placed on the protection cover 20 and electrically connected to the power circuit board 16 for generating heat, and the heating base 10 further comprises a receiving unit 11, the receiving unit 11 center defining said top accommodation open chamber 100, the receiving unit 11 further comprises a heat conductive unit 111 disposed at top accommodation open chamber 100 inner side thereof, the heat conductive unit 111 having one side in contact with one side of the resistor 22, the heat conductive unit 111 reverse side in contact with the aroma capsule 12.

The heat conductive unit 111 can be selected from the material group of metals, ceramics, porcelains or glasses.

In an embodiment, the aroma-diffusing heating device 1 further comprises a light emitting diode circuit board 34 mounted on the bottom cover 142 and electrically connected to the power circuit board 16 for emitting light.

In an embodiment, the receiving unit 11 is made of a material pervious to light, including transparent or translucent plastic, acrylic, glass and light-pervious ceramics.

In an embodiment, the aroma-diffusing heating device 1 further comprises a insulator 23 mounted between the receiving unit 11 and the heat conductive unit 111, for insulate the heat from the resistor 22, heat conductive unit 111 to the receiving unit 11.

Referring to the cross-sectional view of the aroma capsule 12 shown in FIG. 6, as stated above, the aromatic substance 122 is sealed in the aroma capsule 12 and the aroma capsule 12 is accommodated in the top accommodation open chamber 100 of the heating base 10 of the aroma-diffusing heating device 1. When using the aroma-diffusing heating device 1, the user simply needs to remove the sealing film 124 from the heat-transfer container 120 without contacting the aromatic substance 122. Further, after the aromatic substance 122 is used up, the user can put a new aroma capsule in the top accommodation open chamber 100 of the heating base 10 of the aroma-diffusing heating device 1 as a substitute and needs not to wash the heat-transfer container 120 of the used aroma capsule 12. Further, because the user does not need to clean the heat-transfer container 120, the user needs not to worry about breaking down the heat-transfer container 120. Further, the user needs not to prepare a container for holding essential oil. Further, different aroma capsules 12 designed to give off different good smells can be selectively used.

Further, the heat-transfer container 120 is configured to fit the shape of the top accommodation open chamber 100 of the heating base 10 of the aroma-diffusing heating device 1 so that the heat-transfer container 120 can be kept in close contact with the periphery of the top accommodation open chamber 100 of the heating base 10 of the aroma-diffusing heating device 1 to transfer heat energy from the heating base 10 to the aromatic substance 122 rapidly.

In an embodiment, the heating base 10 comprises a top flange 102 protruded from the top wall thereof around the top accommodation open chamber 100. The top flange 102 has the inside wall thereof smoothly downwardly curved toward the top accommodation open chamber 100. Thus, the user can insert the fingers along the smoothly downwardly curved inside wall of the top flange 102 to pick up the aroma capsule 12 from the top accommodation open chamber 100 conveniently. Further, the heat-transfer container 120 defines a rim 1202 around the top opening 1200. The rim 1202 can be configured to extend in a horizontal or vertical manner relative to the elevation of the top opening 1200. Thus, the user can grip the rim 1202 with the fingers to remove the aroma capsule 12 from the accommodation chamber 100 of the heating base 10 of the aroma-diffusing heating device 1 conveniently.

In an embodiment, the aroma-diffusing heating device further comprises a cap 14 capped on the heating base 10 over the aroma capsule 12, the cap 14 has an air vent 140 (or a light vent) for dispersing the aroma of the aromatic substance 122 into the ambient, the cap 14 is made of a material pervious to light, after removal of the sealing film 124 from the heat-transfer container 120.

Figure 8:
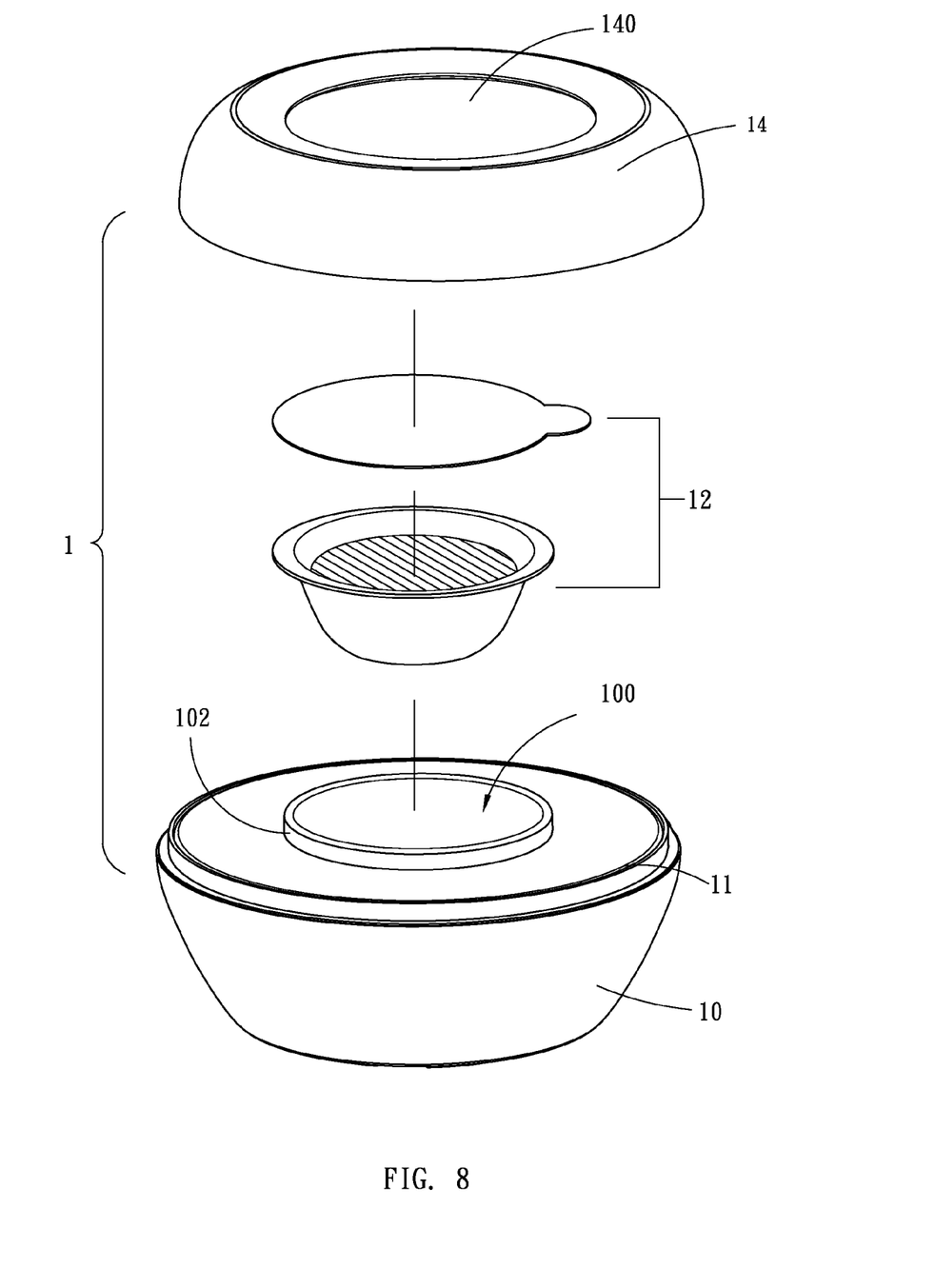
FIG. 8 is an exploded view of an aroma-diffusing heating device in accordance with the present invention.
Figure 9:
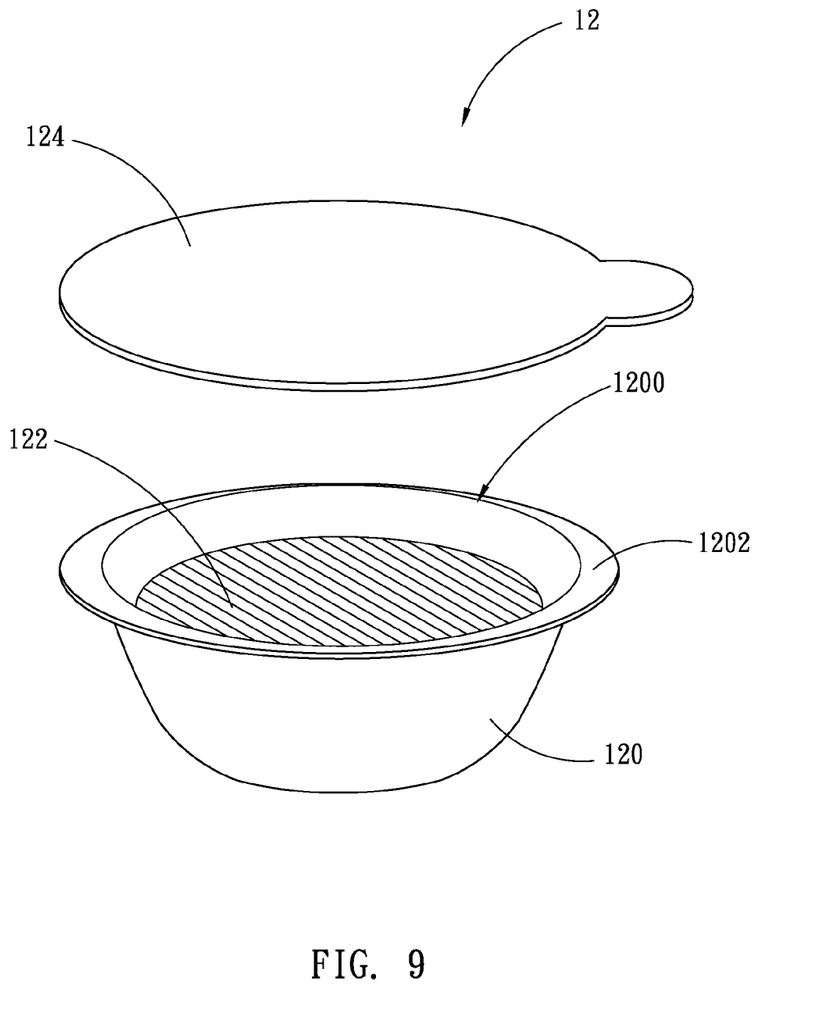
FIG. 9 is an exploded view of the aroma capsule of the aroma-diffusing heating device in accordance with the present invention.
Figure 10:
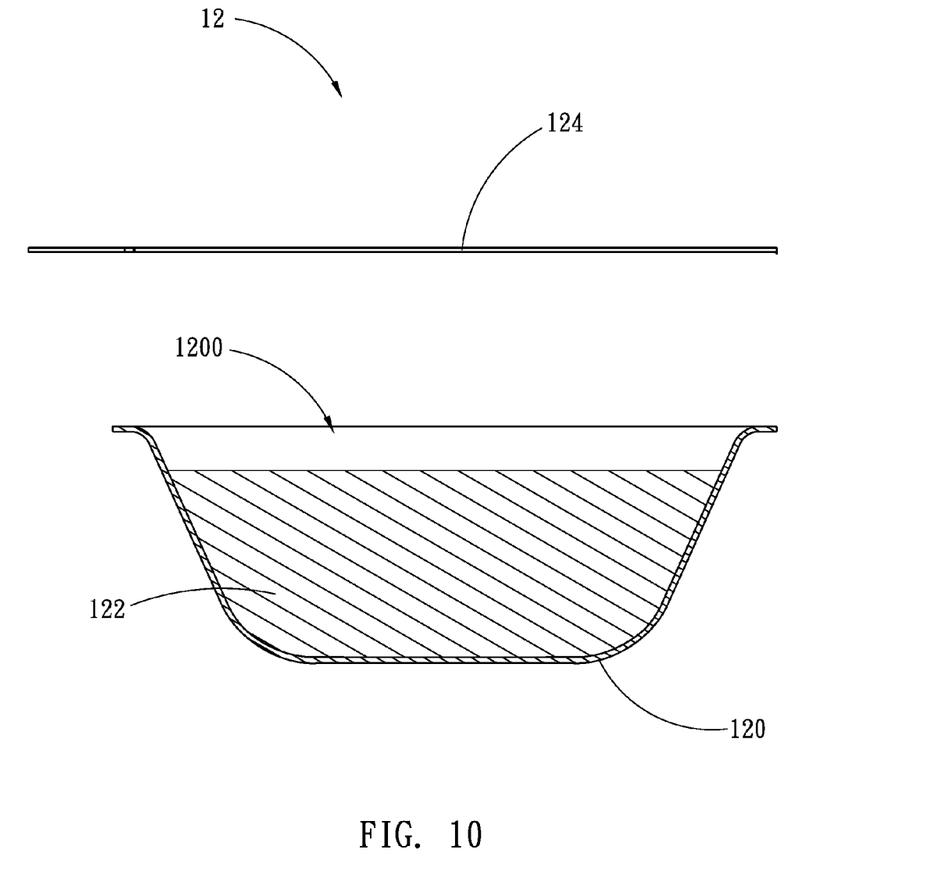
FIG. 10 is a sectional side view of FIG. 9.

FIGS. 8-10 illustrate the aroma capsule 12, comprising: a heat-transfer container 120 defining a top opening 1200; an aromatic substance 122 held in said heat-transfer container 120; and a breathing film 126 bonded to said heat-transfer container 120 over the top opening 1200 of said heat-transfer container 120 above said aromatic substance 122 in said heat-transfer container 120, said breathing film 126 having open spaces defined therein, the aroma substance 122 is heated by aroma-diffusing heating device 1 and disperses scent through the open spaces 1263. It the aroma-diffusing heating device 1 and the aroma capsule 12 are toppled by chance, the melted scented wax is blocked by the breathing film 126 form flowing to a region outside of the aroma-diffusing heating device 1, the aroma-diffusing heating device 1 is thus safe to use.

In an embodiment, the aroma capsule 12 further comprising a sealing film 124 bonded to said heat-transfer container 120 over the top opening to seal said aromatic substance 122 in said heat-transfer container 120 and said breathing film 126 under said sealing film 124.

In an embodiment, the aroma capsule further comprises a rim 1202 extending around said top opening 1200, and said breathing film 126 is bonded to said rim 1202 of the heat-transfer container 120, said aromatic substance 122 is an aromatic wax.

In an embodiment, the aroma capsule 12 further comprising a sealing film 124 bonded to said rim 1202 of the heat-transfer container 120 to seal said aromatic substance 122 in said heat-transfer container 120 and said breathing film 126 under said sealing film 124.

Further, said breathing film 126 has the border edge thereof bonded to said rim 1202 of the heat-transfer container 120.

Alternatively, the border edge 1261 of the breathing film 126 can be bonded to the inside wall of the heat-transfer container 120 above in the top opening 1200.

Further, said aromatic substance 122 is an aromatic wax, fragrant block or balsam.

Referring to FIGS. 8-10, in an embodiment, an aroma capsule 12, comprising: a heat-transfer container 120 defining a top opening; an aromatic substance 122 held in said heat-transfer container 120; and The sealing film 124 bonded to said heat-transfer container 120 to seal said aromatic substance 122 in said heat-transfer container 120.

Figure 1:
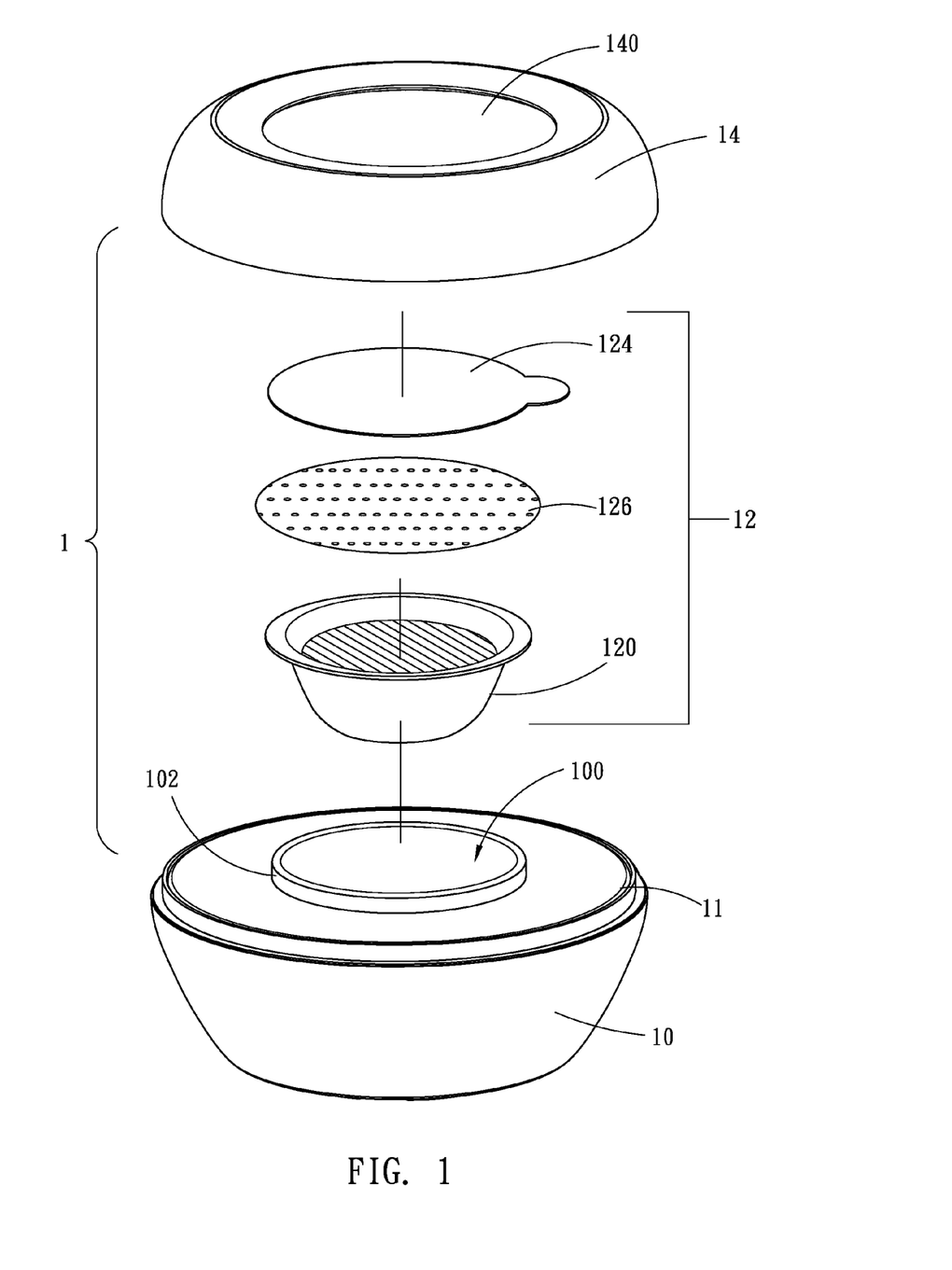
FIG. 1 is an exploded view of an alternate form of the aroma-diffusing heating device in accordance with the present invention.
Figure 2:
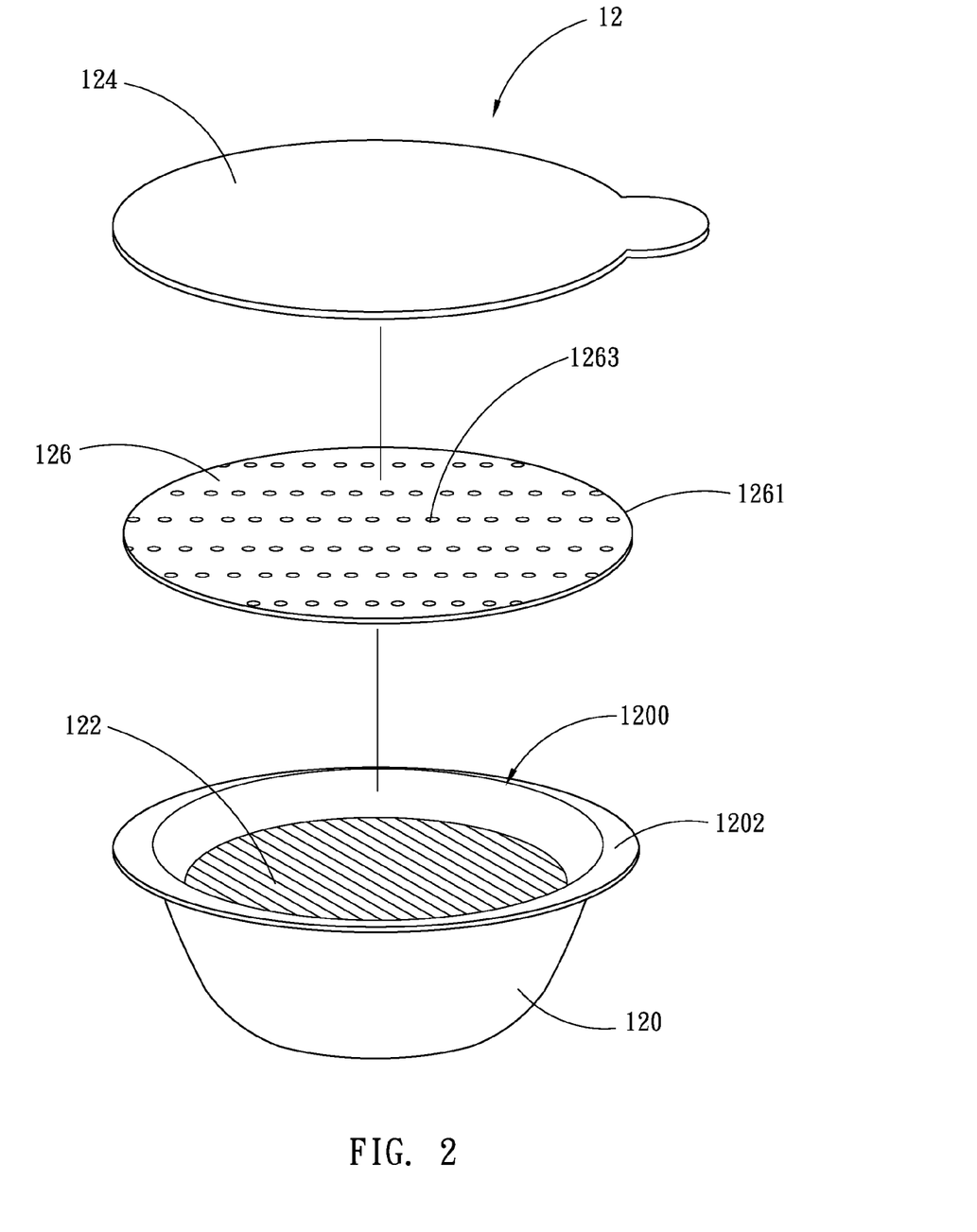
FIG. 2 is an exploded view of the aroma capsule shown in FIG. 1.
Figure 3:
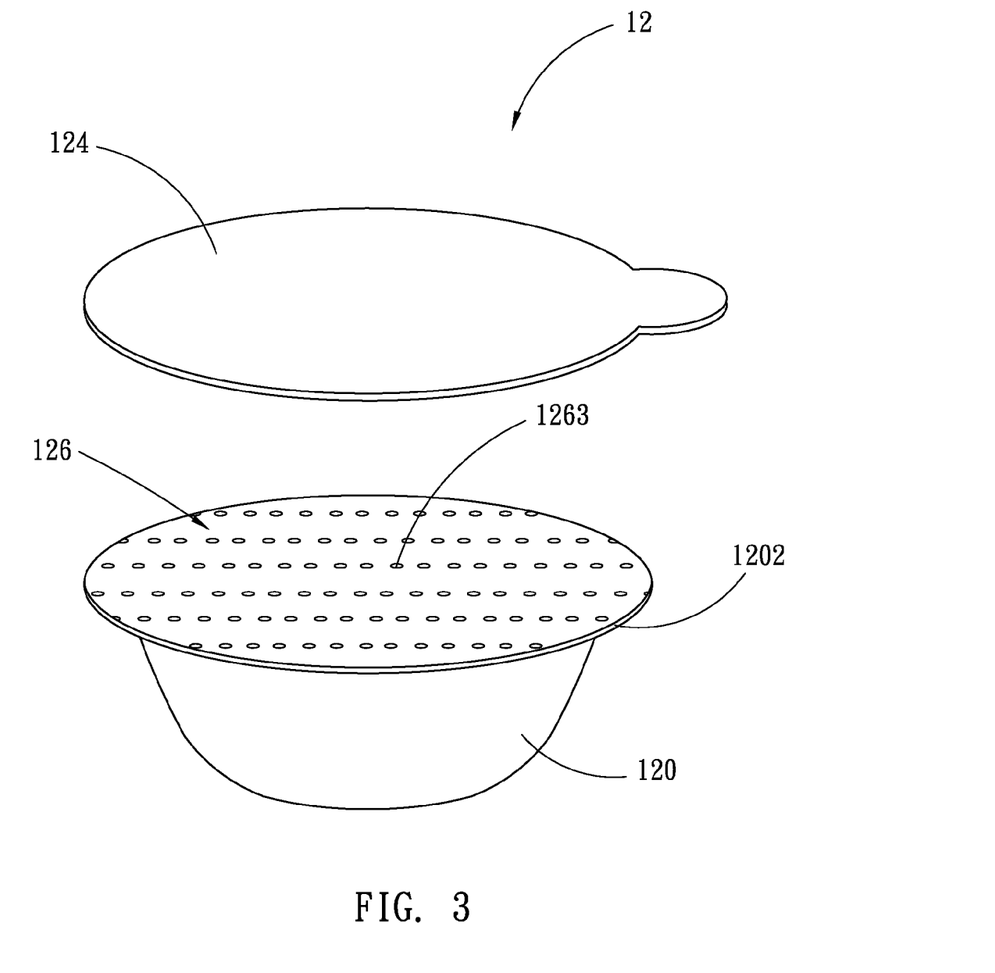
FIG. 3 corresponds to FIG. 2, illustrating the breathing film sealed to the heat-transfer container.
Figure 4:
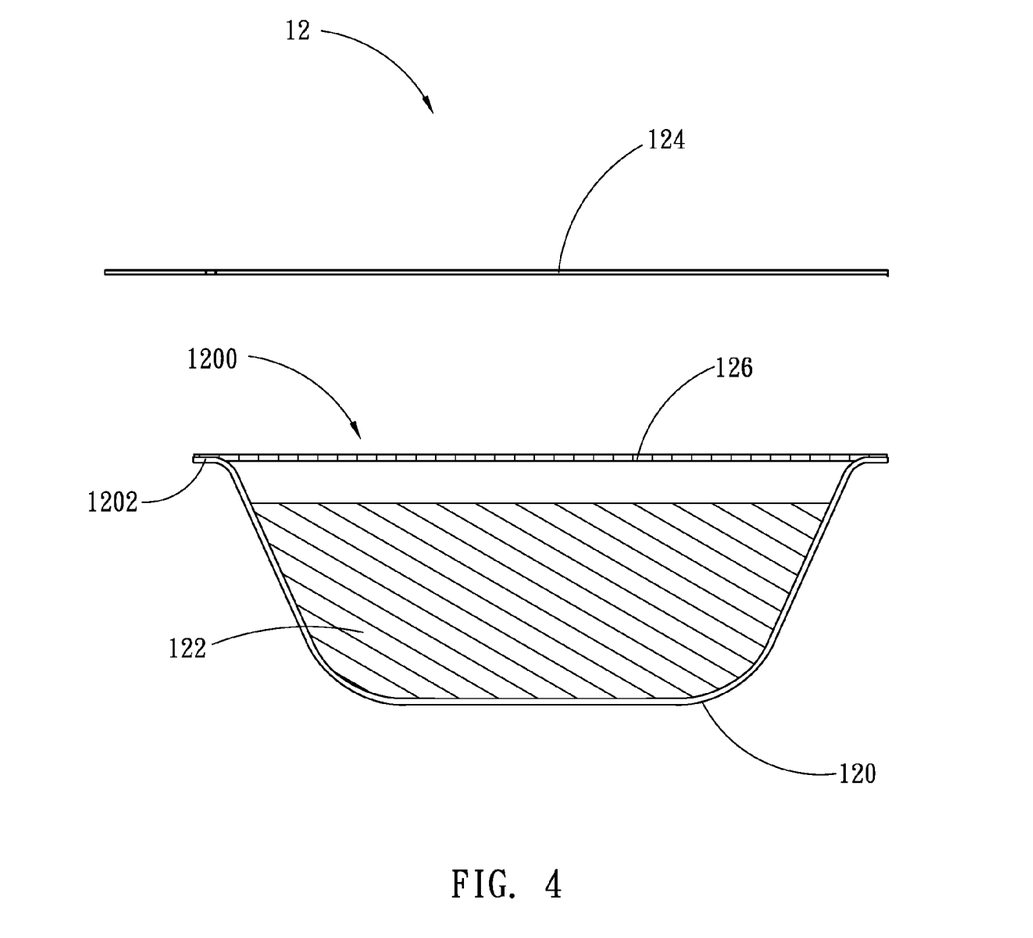
FIG. 4 is a sectional side view of FIG. 3.

Referring to FIGS. 2-4, in an embodiment, the aroma capsule 12, further comprising a breathing film 126 bonded to said heat-transfer container 120 to seal said aromatic substance 122 in said heat-transfer container 120 and said breathing film 126 under said sealing film 124.

When compared to conventional aromatic heating devices, the aroma-diffusing heating device 1 in accordance with the present invention uses a aroma capsule 12 that can be replaced by a new one when used up, and therefore, the user needs not to prepare an extra aroma wax or essential oil container or to worry about breaking down the heat-transfer container, and will not touch the aroma wax or essential oil during replacement of the aroma wax or essential oil.

Although particular embodiment of the invention have been described in detail for purposes of illustration, various modifications and enhancements may be made without departing from the spirit and scope of the invention. Accordingly, the invention is not to be limited except as by the appended claims.

What the invention claimed is:

1. An aroma-diffusing heating device, comprising:
   a heating base comprising a receiving unit defining therein a top accommodation open chamber for receiving an aroma capsule, a heat conductive unit disposed in said top accommodation open chamber for transferring heat to an aroma capsule accommodated in said top accommodation open chamber;
   a bottom cover disposed on a bottom of said heating base;
   a power circuit board disposed on said bottom cover;
   a protection cover supported on said bottom cover;
   a resistor mounted at said protection cover and kept in contact with said heat conductive unit and electrically connected to said power circuit board for generating heat;
   an aroma capsule detachably accommodated in said top accommodation open chamber and heatable by said heat conductive unit to give off fragrance;
   said aroma capsule comprising a heat-transfer container accommodated in said top accommodation open chamber; and
   said heat-transfer container defining a top opening, an aromatic substance held in said heat-transfer container, and a breathing film bonded to said heat-transfer container over the top opening to keep said aromatic substance in said heat-transfer container, said breathing film having open spaces defined therein.

2. The aroma-diffusing heating device as claimed in claim 1, wherein said aroma capsule further comprises a sealing film bonded to said heat-transfer container over the top opening to seal said aromatic substance in said heat-transfer container and said breathing film under said sealing film.

3. The aroma-diffusing heating device as claimed in claim 2, wherein said heat-transfer container of said aroma capsule comprises a rim extending around said top opening, and said sealing film is bonded to said rim of said heat-transfer container.

4. The aroma-diffusing heating device as claimed in claim 1, wherein said heat-transfer container of said aroma capsule further comprises a rim extending around said top opening, and said breathing film has a border edge thereof bonded to said rim of said heat-transfer container.

5. The aroma-diffusing heating device as claimed in claim 4, wherein said breathing film is one selected from the material group consisting of cloth, nonwoven fabric, fiber cloth, woven fabric, porous plastic membrane or porous silicon rubber.

6. The aroma-diffusing heating device as claimed in claim 1, further comprising a cap capped on said heating base over said aroma capsule, said cap comprising an air vent.

7. The aroma-diffusing heating device as claimed in claim 1, wherein said aromatic substance is an aromatic wax.

8. The aroma-diffusing heating device as claimed in claim 1, wherein said heat-transfer container is an aluminum foil bowl.

9. The aroma-diffusing heating device as claimed in claim 1, further comprising a light emitting diode circuit board mounted on said bottom cover and electrically connected to said power circuit board for emitting light.

10. The aroma-diffusing heating device as claimed in claim 9, wherein said receiving unit is made of a light-pervious material selected from the group of transparent and translucent plastics, acrylic, glass and light-pervious ceramics.

11. An aroma capsule, comprising:
a heat-transfer container defining a top opening;
an aromatic substance held in said heat-transfer container; and
a breathing film bonded to said heat-transfer container over the top opening of said heat-transfer container above said aromatic substance in said heat-transfer container, said breathing film having open spaces defined therein.

12. The aroma capsule as claimed in claim 11, further comprising a sealing film bonded to said heat-transfer container over the top opening to seal said aromatic substance in said heat-transfer container and said breathing film under said sealing film.

13. The aroma capsule as claimed in claim 11, wherein said heat-transfer container comprises a rim extending around said top opening, and said breathing film is bonded to said rim.

14. The aroma capsule as claimed in claim 13, further comprising a sealing film bonded to said rim of the heat-transfer container to seal said aromatic substance in said heat-transfer container and said breathing film under said sealing film.

15. The aroma capsule as claimed in claim 13, wherein said breathing film has the border edge thereof bonded to said rim.

16. The aroma capsule as claimed in claim 11, wherein said aromatic substance is an aromatic wax.

17. An aroma capsule, comprising:
a heat-transfer container defining a top opening;
an aromatic substance held in said heat-transfer container; and
a sealing film bonded to said heat-transfer container over the top opening to seal said aromatic substance in said heat-transfer container.

18. The aroma capsule as claimed in claim 17, further comprising a breathing film bonded to said heat-transfer container over the top opening to seal said aromatic substance in said heat-transfer container and said breathing film under said sealing film.

* * * * *